US008366857B2

(12) United States Patent
Hayworth et al.

(10) Patent No.: US 8,366,857 B2
(45) Date of Patent: Feb. 5, 2013

(54) METHODS, APPARATUS AND SYSTEMS FOR PRODUCTION, COLLECTION, HANDLING, AND IMAGING OF TISSUE SECTIONS

(76) Inventors: Kenneth Hayworth, Northridge, CA (US); Amy Au Hayworth, Northridge, CA (US)

( * ) Notice: Subject to any disclaimer, the term of this patent is extended or adjusted under 35 U.S.C. 154(b) by 0 days.

(21) Appl. No.: 12/695,297

(22) Filed: Jan. 28, 2010

(65) Prior Publication Data
US 2010/0323445 A1 Dec. 23, 2010

Related U.S. Application Data

(63) Continuation of application No. 10/886,799, filed on Jul. 8, 2004, now Pat. No. 7,677,289.

(51) Int. Cl.
*B32B 37/22* (2006.01)
*B32B 38/10* (2006.01)
*B32B 38/04* (2006.01)
*B65C 9/04* (2006.01)
*B65C 9/06* (2006.01)
*G01N 1/06* (2006.01)
*B65H 75/00* (2006.01)
*B32B 37/02* (2006.01)
*B65H 75/04* (2006.01)
*B65H 81/02* (2006.01)

(52) U.S. Cl. ........ 156/254; 156/252; 156/253; 156/256; 156/510; 156/517; 156/543; 73/864.41; 435/11

(58) Field of Classification Search ............ 156/252, 156/253, 254, 256, 510, 517, 543, 549; 73/864.41; 435/11
See application file for complete search history.

(56) References Cited

U.S. PATENT DOCUMENTS

| | | | | |
|---|---|---|---|---|
| 4,752,347 A | * | 6/1988 | Rada | 156/382 |
| 5,282,404 A | * | 2/1994 | Leighton et al. | 83/13 |
| 5,746,855 A | * | 5/1998 | Bolles | 156/64 |
| 6,330,348 B1 | * | 12/2001 | Kerschmann et al. | 382/128 |
| 2003/0022271 A1 | * | 1/2003 | Voneiff et al. | 435/40.52 |

FOREIGN PATENT DOCUMENTS
WO   WO 0062035 A1 * 10/2000

* cited by examiner

*Primary Examiner* — Sonya Mazumdar
(74) *Attorney, Agent, or Firm* — Wolf, Greenfield & Sacks, P.C.

(57) ABSTRACT

Methods, apparatus and systems for collecting thin tissue samples for imaging. Thin tissue sections may be cut from tissue samples using a microtome-quality knife. In one example, tissue samples are mounted to a substrate that is rotated such that thin tissue sections are acquired via lathing. Collection of thin tissue sections may be facilitated by a conveyor belt. Thin tissue sections may be mounted to a thin substrate (e.g., by adhering thin tissue sections to a thin substrate via a roller mechanism) that may be imaged, for example, by an electron beam (e.g., in an electron microscope). This tissue sections may be strengthened before cutting via a blockface thinfilm deposition technique and/or a blockface taping technique. An automated reel-to-reel imaging technique may be employed for collected/mounted tissue sections to facilitate random-access imaging of tissue sections and maintaining a comprehensive library including a large volume of samples.

20 Claims, 11 Drawing Sheets

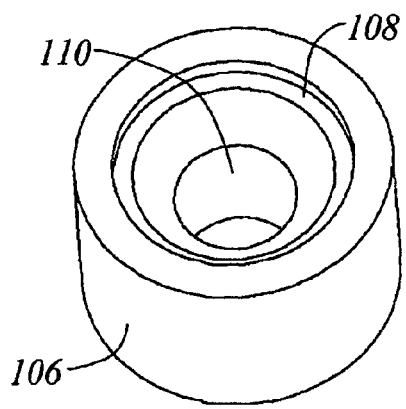
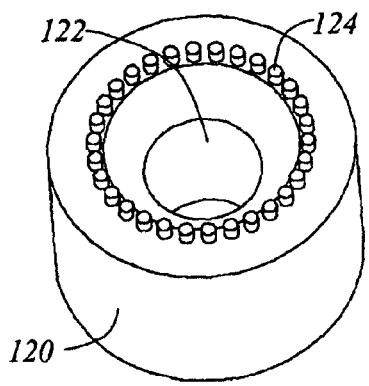
FIG. 1A  FIG. 1B
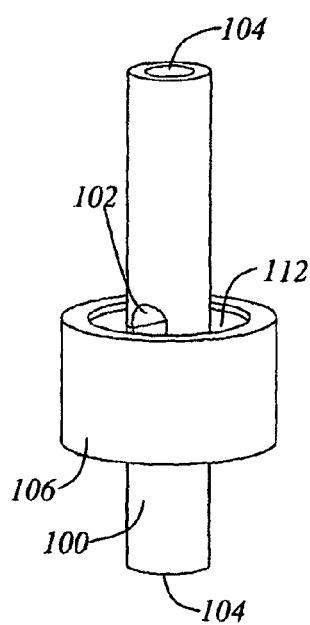
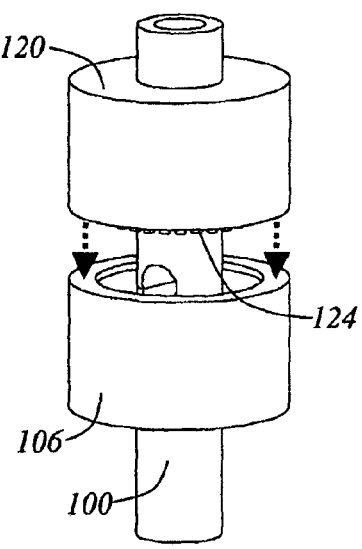
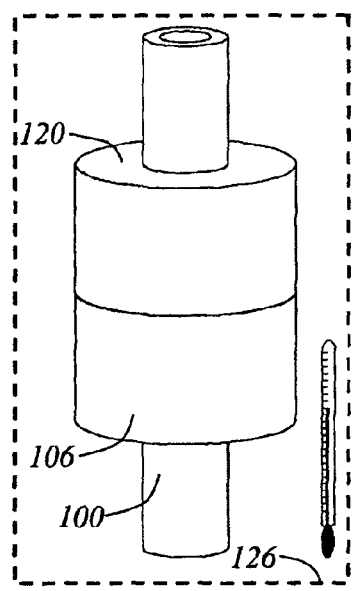
FIG. 1C  FIG. 1D  FIG. 1E

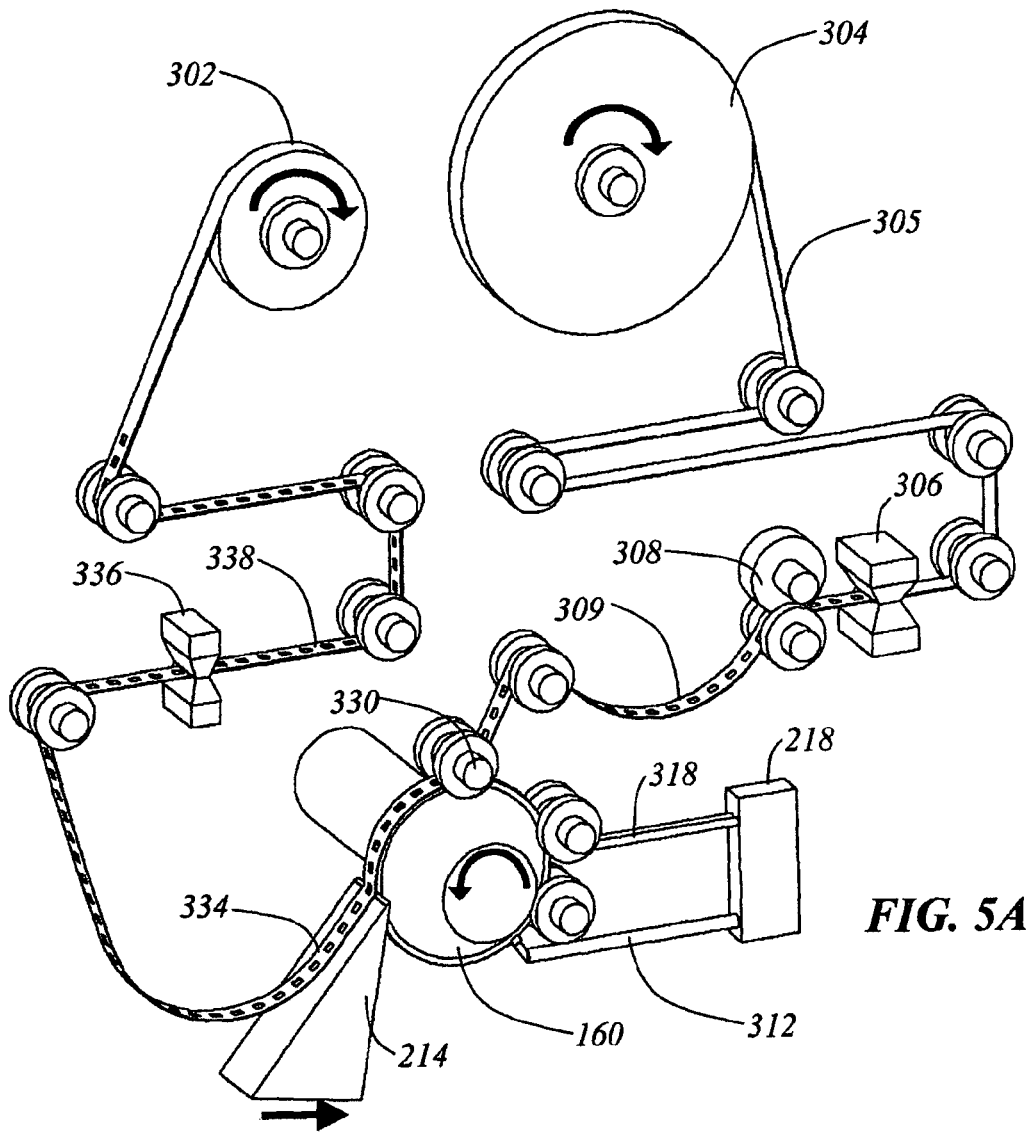
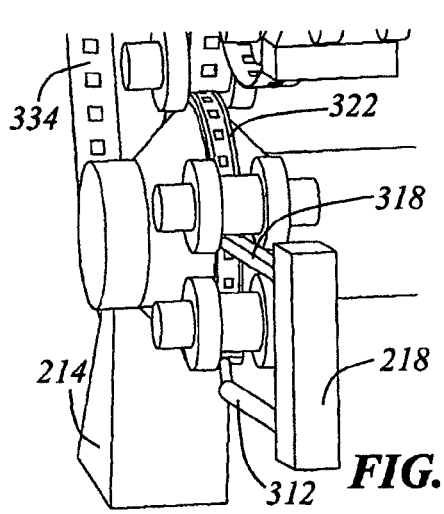
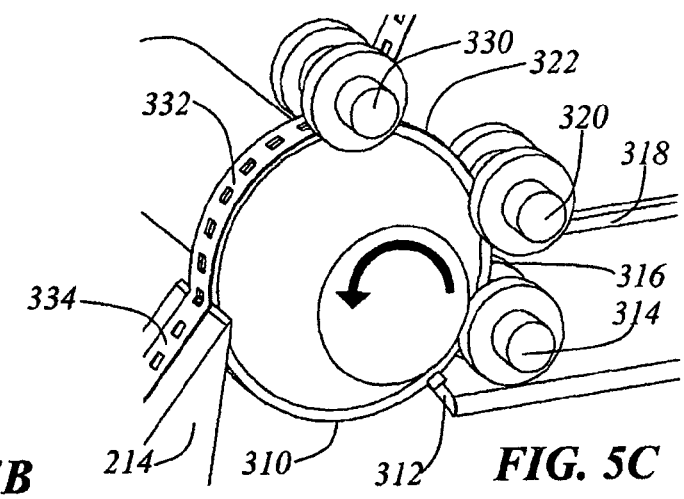

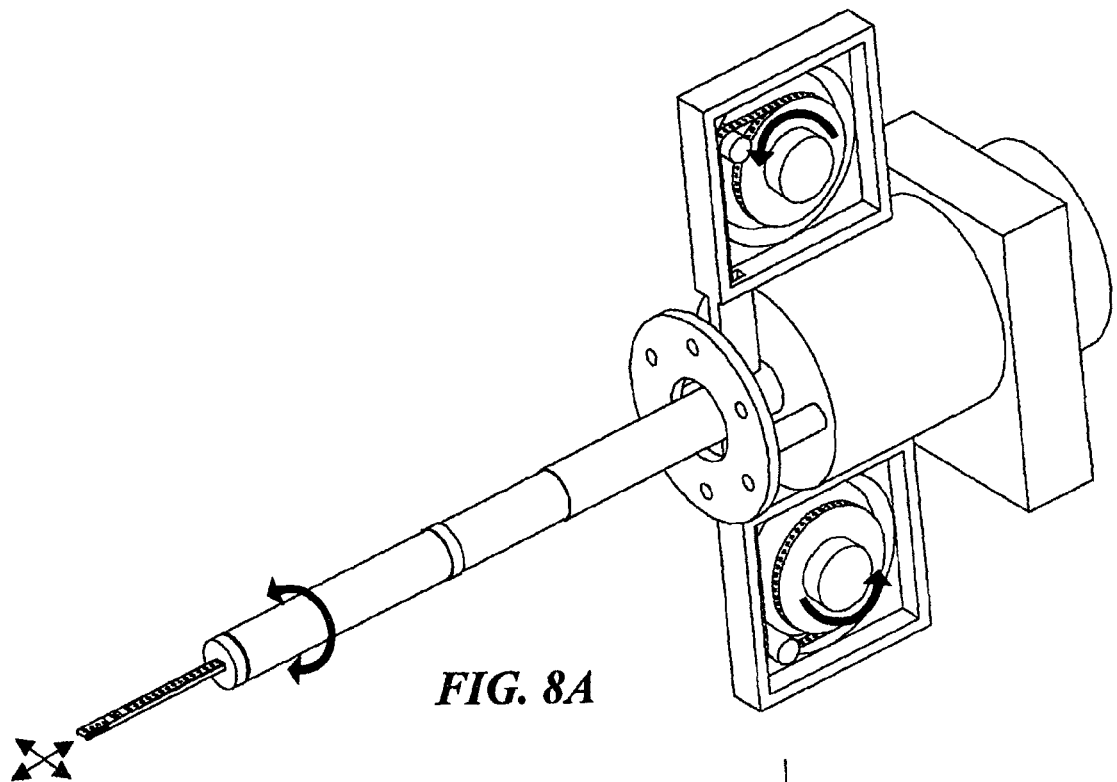
FIG. 8A
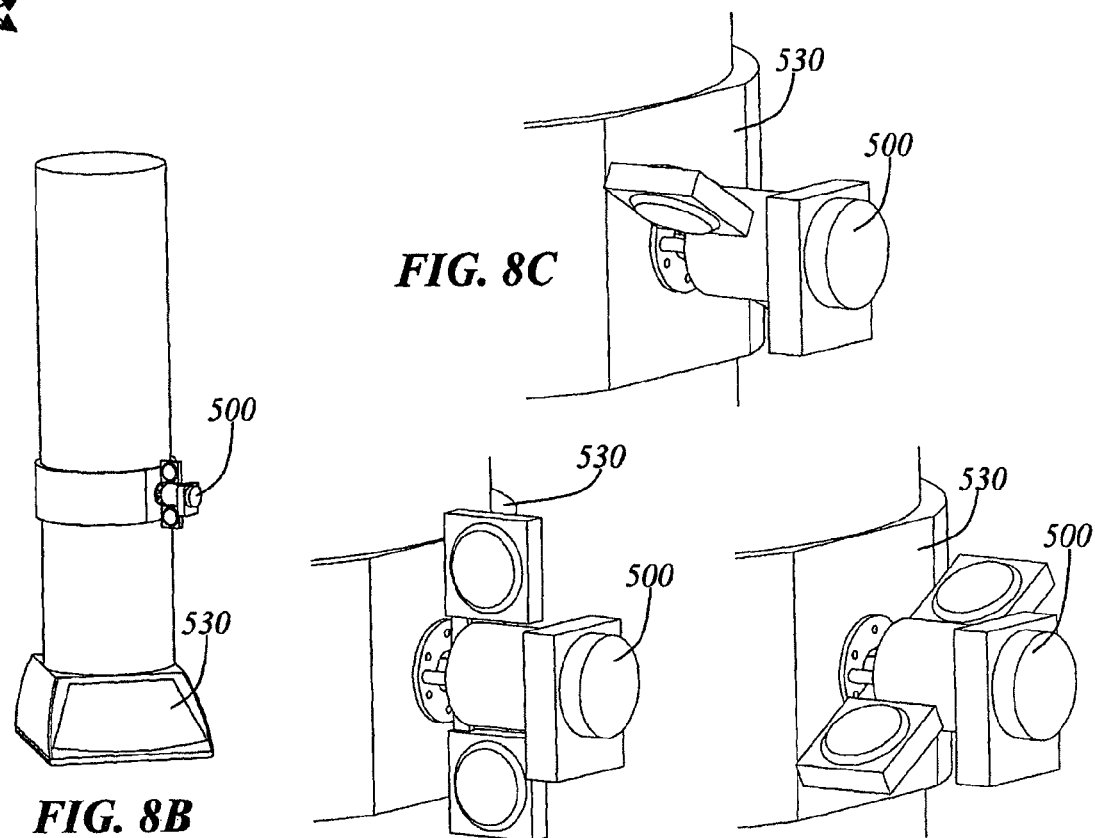
FIG. 8B
FIG. 8C
FIG. 8D
FIG. 8E

METHODS, APPARATUS AND SYSTEMS FOR PRODUCTION, COLLECTION, HANDLING, AND IMAGING OF TISSUE SECTIONS

CROSS REFERENCE TO RELATED APPLICATIONS

This continuation application claims the benefit under 35 U.S.C. §120 of U.S. application Ser. No. 10/886,799, entitled "METHODS AND APPARATUSES FOR THE AUTOMATED PRODUCTION, COLLECTION, HANDLING, AND IMAGING OF LARGE NUMBERS OF SERIAL TISSUE SECTIONS," filed on Jul. 8, 2004, which is hereby incorporated by reference in its entirety.

BACKGROUND OF THE INVENTION

1. Field of Invention

The present invention relates to automating the process of producing thousands of serial tissue sections from an embedded tissue block in such a fashion as to allow said tissue sections to be reliably collected, handled, stored, and digitally imaged (via automated retrieval) using both light and transmission electron microscopes in order to produce 3D reconstructions of the original tissue's structure.

2. Background of the Invention

Today neuroscientists are routinely carrying out evermore-advanced physiological experiments and cognitive scientists are proposing and testing evermore-comprehensive models of brain function. Unfortunately, these experiments and models involve brain systems where incomplete information regarding the system's underlying neural circuitry presents one of the largest barriers to research success. It is widely accepted within the neuroscience community that what is needed is a comprehensive and reliable wiring diagram of the brain that will provide a neuroanatomical scaffolding (and a set of foundational constraints) for the rest of experimental and theoretical work in the neuro- and cognitive sciences. Unfortunately, the current approach of attempting to integrate the deluge of thousands of individual in vivo tracing experiments into a coherent whole is proving to be a virtually impossible task.

There is an alternative approach that avoids the problem of stitching together the results of thousands of in vivo tracer injection experiments. The imaging of a single post-mortem brain at a sufficiently high resolution to resolve individual neuronal processes and synapses, while maintaining registration across size-scales, would allow direct tracing of a brain's connectivity. Researchers using the raw data in such a synapse-resolution brain connectivity atlas would be able to map all the regions, axonal pathways, and synaptic circuits of the brain; and unlike separate specialized experiments, the results would immediately and easily be integrated because they are all performed on the same physical brain.

Today, the creation of such a synapse-resolution atlas has only been achieved for tiny invertebrate animals such as *C. Elegans* (a round worm measuring 1 mm in length and less than 100 μm in diameter). This is because the fundamental technology used, that of serial section electron reconstruction, currently requires the painstaking manual production of thousands of extremely thin (<1 μm) tissue slices using a standard ultramicrotome in which newly sliced tissue sections are floated away from the cutting knife on water and manually placed on slotted TEM specimen grids a few sections at a time.

Because of the manual nature of this current process, this technique is totally impractical to apply to larger brain structures and so it is currently unable to address the needs of the larger community of neuroscientists who require a map of the brain connectivity of rodent and primate brains. The key challenge in extending these imaging technologies to map structures that are $1 \times 10^5$ (mouse brain) and $1 \times 10^8$ (human brain) times as large as *C. Elegans* is the invention of a reliable automated process for producing these thin serial tissue sections. The invention described herein is targeted at this automation challenge.

3. Prior Art

We are unaware of any current microtome design (either in production or disclosed in the open literature) that adequately addresses this need for automating the production, collection, handling, and imaging of large numbers of thin tissue sections suitable for use in light and transmission electron microscopic 3D reconstruction work. Although there is a vast number of patents pertaining to microtomes and their automation, these designs are targeted toward automating the slicing process only, and do not address the tissue collection and handling processes. Today the term "automated microtome" has become synonymous with a manual microtome merely having motorized knife advance. Thus, current "automated microtome" designs still require manual slice retrieval and manual slide or grid mounting for imaging. Such manual slice retrieval necessitates skilled, delicate, and incredibly time-consuming work be expended on each tissue slice (or small series of slices) as it involves "fishing" each tissue slice out of a water boat attached to the knife of the ultramicrotome instrument and onto a TEM grid.

One published microtome design that does somewhat address the automation of tissue collection is U.S. Utility Pat. No. 5,746,855 by Bolles. In that design, the standard manual method of blockface taping (whose advantages for slice collection and handling are described more fully in U.S. Utility Pat. No. 4,545,831 by Ornstein) is proposed to be automated by a pressure roller pressing a reel of transparent adhesive tape against the blockface just before the microtome blade cuts the next slice of tissue off the block. Thus the slice is adhered to the tape and can be carried away automatically by simply advancing the tape reel. (The advantages of tape as a collection, storage, and imaging medium for tissue sections is described in U.S. Utility Pat. No. 3,939,019 by Pickett.)

The automatic taping lathe-microtome invention described herein is most similar to this taping designed proposed by Bolles; however, our design improves and extends the application of that design significantly. For example, a key disadvantage of Bolles' design is that it makes no modification to the current standard microtome design which involves a discontinuous ratcheting motion of the flat block across the knife. Thus the Bolles design requires the tape to be freshly applied to the block after each slice also in a discontinuous fashion. This seems difficult to automate reliably especially for very thin tissue slices as would be required for most neural reconstruction work.

Another proposed method for automating the collection of tissues from a microtome disclosed in U.S. Utility Pat. No. 6,387,653 by Voneiff and Gibson, proposed the use of a series of rollers to collect the tissue from the blade of a microtome and move it directly to a glass slide. That design also makes no modification to the current standard microtome design, and thus also suffers from the discontinuous ratcheting action. The Voneiff and Gibson design, however, uses neither blockface taping nor tape as a collection medium.

It should be noted that neither the Bolles' design nor the Voneiff and Gibson design target the collection of tissue slices for electron microscopic (ultrastructure) imaging. Imaging by an electron beam requires that the tissue slice is unobstructed by any holding substrate thicker than a few nanometers. The tape in Bolles' design and the glass slide in the Voneiff and Gibson design are much too thick for this. The design disclosed herein directly targets collection of slices for light and transmission electron microscopic imaging, and makes modifications to the tape collection medium in order to accommodate this.

The automatic taping lathe-microtome invention described herein completely redesigns the basic cutting motion of the microtome, replacing the standard discontinuous ratcheting motion with the continuous rotary motion of a lathe. As will be described below, this continuous lathe cutting design makes possible continuous taping and slice collection. The result is a mechanically more stable, more reliable, faster, and more easily constructed design which should finally make possible the fully automated production, collection, handling, imaging, and storage of thousands of semithin and ultrathin tissue sections for use in light and transmission electron microscopic serial 3D reconstruction of neural (and other) tissue.

SUMMARY OF THE INVENTION

The central invention described herein, the "automatic taping lathe-microtome", produces a continuous ribbon of tissue by lathing an extremely thin strip off the surface of a cylindrical block containing a multitude of embedded tissue samples. The automatic taping lathe-microtome includes mechanisms for sandwiching and adhering this thin and fragile ribbon of tissue between a pair of supporting top and bottom base tapes. One of these base tapes is adhered to the ribbon of tissue before the ribbon is lathed from the block (using a blockface taping method) and the other base tape is adhered after the ribbon is lathed off. If the top and bottom base tapes are composed of transparent material, the resulting composite tape-sandwich allows for light microscopic imaging of the tissue sections while providing complete environmental protection of the fragile tissue sections by hermetically sealing them between the top and bottom base tapes. If, on the other hand, special holes are cut in the top and bottom base tapes above and below each tissue slice (holes cut either before or after the lathing action) then the tissue sections will be framed by the supporting base tapes but the view of these tissue sections will remain unobstructed by the base tapes. Such hole-cut base tapes can then act as TEM slot grids and allow for direct viewing of each tissue slice in a standard transmission electron microscope (TEM).

Such TEM-ready composite tape-sandwiches are designed to be mounted on reels within an "electron tomography tape cassette", a related invention disclosed herein. This tape cassette is hermetically sealed and is designed to allow direct coupling to a standard TEM's specimen port sharing its vacuum. Any tissue section of the composite tape-sandwich can thus be reeled into the electron beam of the TEM much like the film in a movie projector. This allows for random-access imaging of any section on the tape (each tape perhaps containing tens of thousands of serial sections representing an equivalent of several cubic millimeters of brain volume) all without requiring the vacuum seal on the TEM to be broken. Cassettes include tape drive motors, positioning clamps and motors, and a precision tomographic tilt motor for 3D electron tomography. This combined system of the automatic taping lathe-microtome, the TEM-ready composite tape-sandwich, and the electron tomography tape cassette is intended to make possible the efficient creation of synapse-resolution brain connectivity atlases for the neuroscience research community.

BRIEF DESCRIPTION OF THE DRAWINGS

In all drawings like reference numbers represent corresponding parts throughout:

FIG. 1A is a perspective view of the bottom silicone rubber mold.

FIG. 1B is a perspective view of the toothed silicone rubber mold.

FIGS. 1C, 1D, and 1E are a series of perspective views showing the first three sequential steps in the tissue embedding process.

FIG. 5A is a perspective view detailing the tape-web mechanism and cylindrical tissue block (with lathe body removed).

FIG. 5B is a close-up view from the back of the tissue block. This view details the blockface applicator mechanisms.

FIG. 5C is a close-up view of the side of the tissue block during operation of the automatic taping lathe-microtome.

FIG. 8A is a perspective view of the electron tomography tape cassette with arrows drawn to display the main degrees of freedom of movement allowed by the mechanism.

FIG. 8B depicts a stylized transmission electron microscope (TEM) with the electron tomography tape cassette inserted into its specimen port.

FIGS. 8C, 8D, and 8E are three close-up views of the electron tomography tape cassette detailing how the entire cassette mechanism can rotate relative to the TEM in order to perform a tomographic tilt-series on the tissue sample at the tip.

DRAWINGS—REFERENCE NUMERALS

Figure 2A:
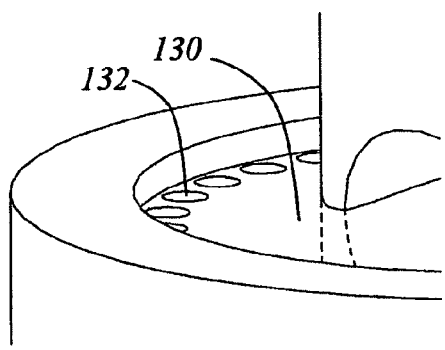
FIG. 2A is a close-up view of the tooth-indentation cavities.

- 100—Axle
- 102—Central hole in axle
- 104—Center-drilled ends of axle
- 106—Silicone rubber bottom embedding mold
- 108—Mold cavity (of part 106)
- 110—Axle seal hole (of part 106)
- 112—Liquid embedding resin
- 120—Silicone rubber toothed embedding mold
- 122—Axle seal hole (of part 120)
- 124—Mold teeth (count of 30)
- 126—Schematic of curing oven
- 130—Partially cured embedding resin
- 132—Tooth-indentation cavities (count of 30)
- 140—1 mm$^3$ tissue cube (count of 27)
- 150—Silicone rubber top embedding mold
- 152—Axle seal hole (of part 150)
- 154—Resin fill-ports (of part 150)
- 160—Axle-mounted cylindrical tissue block
- 162—Part of tissue block without tissue cube (count of 3)
- 200—Automatic taping lathe-microtome
- 201—Lathe body
- 202—Lathe headstock spindle bearing
- 204—Lathe tailstock with live center
- 206—Lathe spindle and belt drive
- 208—Precision DC gearhead motor
- 210—Precision linear translation stage
- 212—Precision linear motorized actuator
- 214—Microtome knife
- 216—Lathe dog
- 218—Film and adhesive blockface-application mechanism
- 300—Tape-web assembly
- 301—Tape (full web)
- 302—Final composite tissue tape-sandwich take-up reel
- 304—Top base tape feed roll
- 305—Top base tape (unprocessed)
- 306—Tape hole puncher mechanism
- 308—Tape drive rollers
- 309—Web slack region before blockface taping
- 310—Freshly cut surface of cylindrical tissue block
- 312—TEM support film applicator head
- 314—TEM support film smoothing and drying roller mechanism
- 316—Block surface with TEM support film
- 318—Adhesive strip applicator heads (count of 2)
- 320—Adhesive strips smoothing and drying roller mechanism
- 322—Block surface with TEM support film and adhesive strips
- 330—Blockface taping pressure roller
- 332—Section of top base tape adhered to blockface
- 334—Freshly microtomed ribbon of tissue adhered to top base tape
- 336—Bottom base tape applicator (print head) and blow-out hole mechanism
- 338—Final TEM-ready composite tissue tape-sandwich (abbreviated: tissue tape)
- 400—Single microtomed tissue slice (1 mm$^2$, 100 nm-1 µm thick)
- 402—Ribbon of tissue slices in embedding medium
- 404—TEM support film coating
- 406—Adhesive strips
- 408—Top base tape
- 409—Viewing hole cut in top tape directly over tissue slice
- 410—Bottom base tape
- 411—Viewing hole cut in bottom tape directly over tissue slice
- 500—Electron tomography tape cassette
- 502—TEM mounting flange
- 504—TEM specimen stage body (vacuum seals to TEM)
- 506—Cassette reels and drive motors (count of 2) for tissue tape
- 508—TEM sample stage tip mechanism
- 510—Tissue slice clamped in position for TEM imaging
- 512—Tomography tilt-series drive motor
- 520—Tissue tape image-securing top clamps (count of 2)
- 521—Tissue tape image-securing bottom clamps (count of 2)
- 522—Blowout hole in wrap-around portion of tissue tape
- 524—Blowout hole tape length adjust pulley
- 530—Transmission electron microscope (TEM)
- 600—Water boat for tissue collection
- 602—Water
- 610—Partially-submerged conveyor-belt
- 612—Submerged pulley
- 614—Bottom base tape hole puncher
- 616—Pressure roller
- 618—Tape-sandwich sealing mechanism

DETAILED DESCRIPTION OF THE PREFERRED EMBODIMENT

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Overview

The present invention discloses a device, an automated taping lathe-microtome, and a set of associated methods and apparatuses for fully automating the collection, handling, and imaging of large numbers of serial tissue sections. In order to most clearly describe these methods and apparatuses I will first briefly outline the current method of producing serial tissue sections for TEM (transmission electron microscopic) imaging.

Current State-of-the-Art

Classical TEM tissue processing and imaging methods begin by embedding an approximately 1 mm$^3$ piece of biological tissue that has been fixed with mixed aldehydes, post-fixed with osmium tetroxide, and infiltrated with an embedding resin. This single tissue cube is then placed in a silicone rubber mold which is then filled with liquid embedding resin. The mold is placed in an oven in order to cure the resin and tissue into a hard tissue block. This tissue block is then clamped in the chuck of a microtome (for TEM use this is also called an ultramicrotome).

This chuck is mechanically actuated to allow the tissue block to be driven down in a smooth trajectory across a very sharp knife thus liberating a slice of the embedded tissue suitably thinned to allow TEM imaging. In "sliding" and "rotary" microtome designs the chuck is moved along a linear trajectory across the blade. (The rotation in a "rotary" microtome is referring to a crank wheel that is rotated by the operator. That rotation is converted to a linear motion of the chuck.) In a "disc" microtome (see U.S. Utility Pat. No. 6,253,653) the trajectory of chuck movement is along a circular arc; however, the sliding, rotary, and disc microtomes' motions are all inherently saltatory using a discontinuous ratcheting motion where the knife engages and disengages the tissue block every slice. Sequential tissue sections are produced by ratcheting the chuck forward toward the knife a small distance after each slice.

The resulting thin tissue slices are typically less than 1 µm thick and are extremely fragile. In fact, they are so fragile that they would be destroyed if one attempted to remove them from the bare surface of the knife which produced them. For this reason, the knife has a boat of water attached to it in such a manner as to allow newly cut tissue to float on the water (supported by surface tension) immediately subsequent to its cutting from the tissue block. This technique protects the fragile tissue section from friction induced mechanical damage which would occur from extended contact with the knife's body. A histology technician then manually scoops the floating tissue section (or short series of sections) onto a slotted TEM specimen grid, one whose slot opening has been previously coated with an ultra-thin film of plastic TEM support film. This support film is strong enough to provide support for the tissue section bridging the slot's gap, but still thin enough to allow unobstructed TEM viewing.

To image this tissue section, the specimen grid is placed in a TEM specimen stage and manually inserted into the vacuum port of a TEM. Vacuum is pulled on the TEM, and the specimen is finally imaged via the TEM's electron beam. Reliably producing, collecting, and imaging thousands of serial sections from a single block is required to reconstruct even cubic millimeter-sized volumes of neural tissue, and this is virtually impossible to accomplish using these classical methods and microtome designs.

Key Innovations Disclosed Here

The innovations disclosed here are designed to bring a high degree of automation to this entire process of tissue collection, handling, and imaging; thus allowing the mass production of serial sections for large-volume 3D reconstruction research. This automated mass production is accomplished by the following innovations to the classical methods and microtome designs:

Innovation #1: Embed multiple tissue cubes in a single block and process them all at the same time.

Innovation #2: Use an axle-mounted cylindrical tissue block and continuous lathe slicing motion (instead of the traditional discontinuous ratcheting motion of current sliding, rotary, and disc microtome designs).

Innovation #3: Strengthen the tissue sections before cutting by use of blockface thinfilm deposition and blockface taping, thus making subsequent steps more reliable.

Innovation #4: Collect tissue sections by the thousands via a tape-sandwich that doubles as a durable handling and storage medium, as well as a TEM imaging specimen grid.

Innovation #5: Load entire tissue-tape (containing thousands of serial sections) into the electron microscope all at once, threading the tape through the electron beam in a fashion similar to film in a movie projector. This allows random-access imaging of any tissue section on the entire tape without forfeiting the time needed to crack the TEM's vacuum and re-pumping.

The preferred embodiment of these innovations will now be described in the following logical order:
1. Description of the axle-mounted cylindrical tissue block embedding method and mold tooling.
2. Description of the automatic taping lathe-microtome mechanical design and operation.
3. Description of the electron tomography tape cassette mechanical design and operation.

Axle-mounted Cylindrical Tissue Block Embedding Method and Tooling

FIG. 1A shows a silicone rubber embedding mold 106, having a cylindrical cavity 108, and a central hole 110. FIG. 1C shows how the mold 106 is slipped onto a metal axle 100 such that the hole 108 forms a liquid-tight seal against the axle 100. The axle 100 has center-drilled ends 104 for eventual mounting on a lathe. In the first step of the embedding process depicted in FIG. 1C, liquid embedding resin 112 is poured into mold 106 to fill it halfway. The axle 100 has a central hole 102 which is also filled by the resin 112.

FIG. 1B shows a toothed silicone rubber mold 120. This mold also has a central hole 122 which forms a seal with the axle 100. The toothed silicone rubber mold 120 has a multitude of protruding teeth 124. FIG. 1D depicts the second step of the embedding process. The toothed silicone rubber mold 120 is slipped onto the top of the axle 100 such that the teeth 124 become immersed a set distance into the liquid embedding resin 112. A repeatable depth of immersion of the teeth 124 into the resin 112 is guaranteed when the toothed mold 120 is pressed against the bottom mold 106 such that they form a tight seal.

FIG. 1E depicts the third step of the embedding process. The axle 100 with filled molds 106 and 120 are placed in a curing oven schematically depicted by a rectangle and thermometer symbol 126. The axle is left in the oven until the resin is partially cured.

Figure 2B:
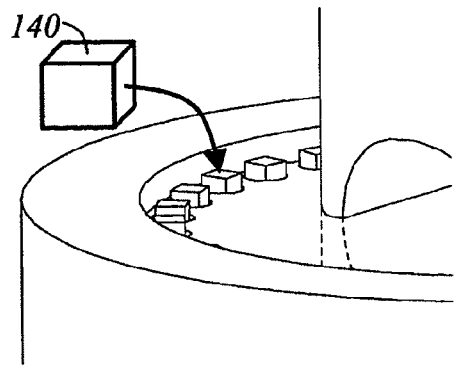
FIG. 2B is a close-up view of tissue cubes being placed in the tooth-indentation cavities.
Figure 2C:
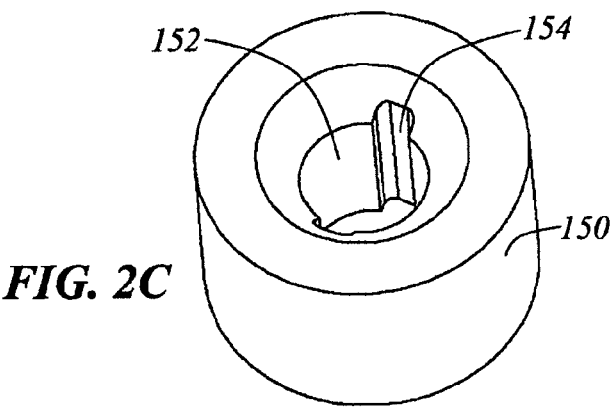
FIG. 2C is a perspective view of the top silicone rubber mold.
Figure 2D:
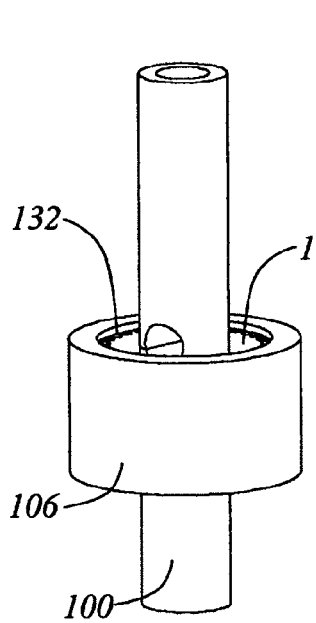
FIGS. 2D, 2E, and 2F are a series of perspective views showing the fourth, fifth, and sixth steps in the tissue embedding process.
Figure 2E:
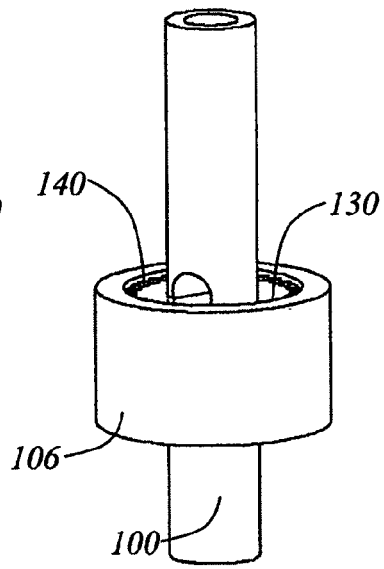

FIG. 2A (close-up) and FIG. 2D depict the fourth step of the embedding process where the toothed mold 120 is removed after curing to reveal a partially cured embedding resin 130 having a multitude (count of 30) of tooth-indentation cavities 132. In FIG. 2B (close-up) and FIG. 2E, the fifth step of the embedding process, a multitude of tissue cubes 140 are manually placed into some, but not all, of the tooth-indentation cavities 132. A total of 27 tissue cubes are inserted into the tooth-indentation cavities leaving three cavities free of tissue. Each of these tissue cubes 140 have been previously been fixed with mixed-aldehydes, post-fixed with osmium tetroxide, en bloc stained with heavy metals, and infiltrated with resin as per standard TEM tissue processing procedures. The tooth-indentation cavities 132 provide a means to secure the tissue cubes 140 in a set orientation and position with respect to each other and to the axle 100 throughout the rest of the embedding process.

FIG. 2C shows a silicone rubber top mold 150. This mold is also designed to slip onto axle 100 via a hole 152 in the center of the mold 150. Two resin fill-ports 154 ensure that the hole 152 does not make a complete seal with the axle 100, but instead leaves a path for resin filling.

Figure 2F:
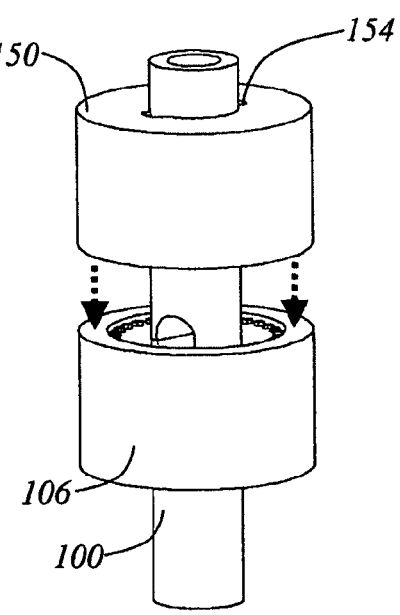

FIG. 2F depicts the sixth step of the embedding process where the top mold 150 is slipped onto axle 100 and pressed into contact with bottom mold 106 such that the two form a liquid-tight seal against each other. Thus they together form a single tissue embedding mold cavity.

Figure 3A:
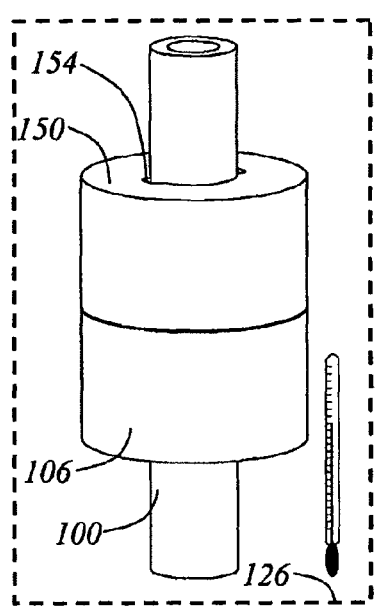
FIGS. 3A and 3B are perspective views showing the last two steps in the tissue embedding process.
Figure 3B:
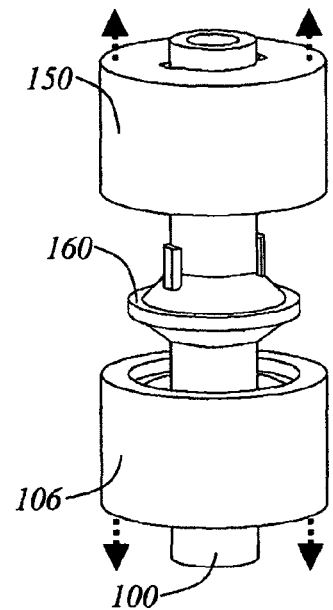

In step seven of the embedding process, depicted in FIG. 3A, new liquid resin is poured into one of the resin fill-ports 154 and air is allowed to escape through the other fill-port 154. Enough resin is poured in to fill up the entire cavity of molds 106 and 150. This assembly of axle 100 is then placed in curing oven 126 and allowed to completely cure. Removal of the top mold 150 and the bottom mold 106 is depicted in FIG. 3B. This reveals a completely cured axle-mounted cylindrical tissue block 160. If necessary, excess pieces of cured resin or inaccuracies in block shape can be removed or corrected by lathing down the sides of the axle-mounted cured cylindrical tissue block 160 at this step using a standard commercial lathe.

Figure 3C:
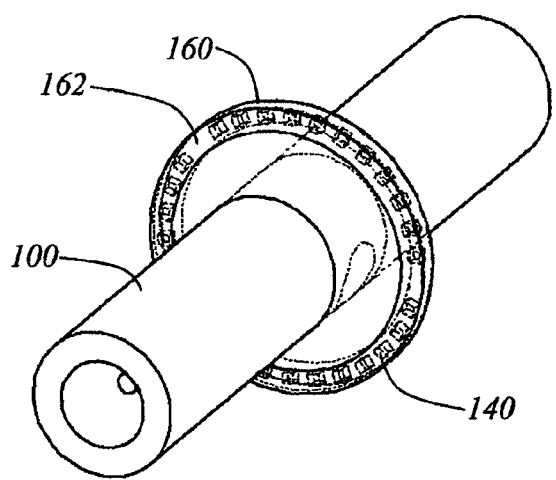
FIG. 3C is an enlarged view of the final cured axle-mounted cylindrical tissue block.

FIG. 3C show a more detailed view of the axle-mounted cylindrical tissue block 160. The 27 embedded tissue cubes 140 are seen populating the circumference of the cylindrical tissue block. Three empty spots in this circumference 162 are also depicted (these empty positions along the circumference will be used later for "blowout hole" slots needed during the imaging processes). The automatic taping lathe-microtome described next will shave a thin spiral ribbon off the circumference of this block and mount that ribbon between protective base tapes. Every full rotation of the axle-mounted tissue block 160 within the automatic taping lathe-microtome will liberate a short stretch of ribbon containing 27 slices of the tissue cubes embedded within. A few thousands of revolutions will liberate a very long ribbon, and will have succeeded in reducing all 27 1 mm³ tissue cubes into a tape containing thousands of thin tissue slices suitable for light or TEM imaging and 3D reconstruction work.

Figure 3D:
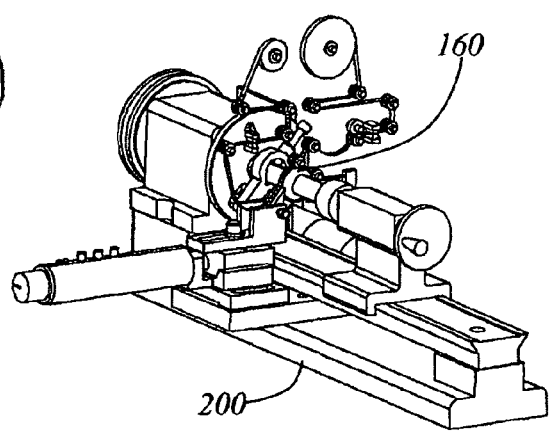
FIG. 3D is a view showing where the axle-mounted tissue block gets inserted in the automatic taping lathe-microtome.

In FIG. 3D shows the position where the axle-mounted cylindrical tissue block 160 is mounted within the automatic taping lathe microtome 200.

Automatic Taping Lathe-microtome Mechanical Design and Operation

Figure 4A:
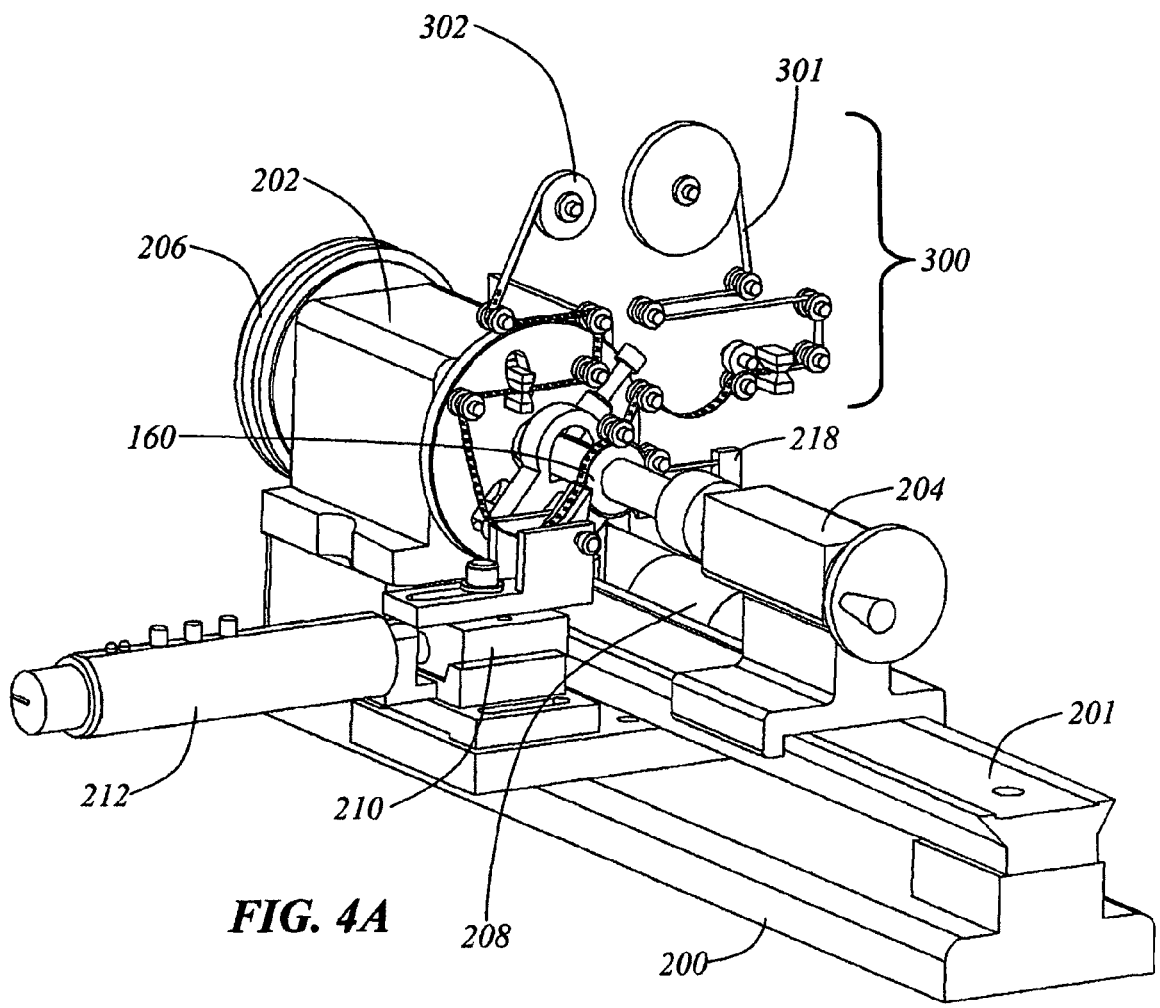
FIG. 4A is a perspective view showing the preferred embodiment of the automatic taping lathe-microtome. The supporting housing of the taping mechanism is removed in this and following figures to better display the mechanism.
Figure 4B:
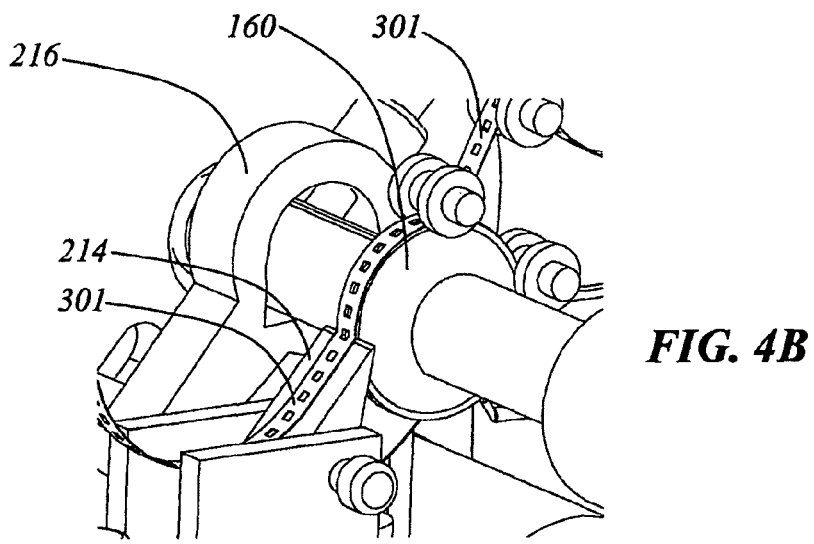
FIG. 4B is a close-up view of where the knife cuts the tissue block in the automatic taping lathe-microtome.

FIG. 4A is a perspective drawing of the automatic taping lathe-microtome 200 depicting all of its main component parts except those associated with the tape-web assembly 300 which is detailed later in FIG. 5A. FIG. 4B is a close-up view of the microtome knife 214 cutting the axle-mounted cylindrical tissue block 160. The main body of the automatic taping lathe-microtome 200 is a small jeweler's lathe 201 having a standard headstock spindle bearing 202, and tailstock with live center 204. The axle-mounted cylindrical tissue block 160 is mounted between the headstock spindle bearing 202 and the tailstock 204 using the center-drilled ends 104 of axle 100. A lathe dog 216 is attached to the axle 100 of the cylindrical tissue block 160 such that the lathe spindle and belt drive 206 can drive the axle-mounted cylindrical tissue block 160 in a rotary motion. The lathe spindle and belt drive 206 is driven by a precision DC gearhead motor 208 at a slow and steady rate setting the pace of the rest of the automatic taping lathe-microtome's mechanisms.

On the side of the lathe body 201 the standard lathe cross-slide has been replaced by a precision linear translation stage 210. This stage is driven by a precision linear motorized actuator 212 which is capable of providing the sub-micron movements necessary for TEM microtomy. Attached to the linear translation stage 210 is the microtome knife 214. This assembly enables the knife 214 to be slowly pressed against the rotating cylindrical tissue block 160 in a lathe-like fashion thus liberating a ribbon of tissue into the tape-web assembly 300. The tape-web assembly 300 holds the tape 301 inline with the rotating cylindrical tissue block 160 such that blockface taping can proceed at a continuous rate in synchrony with the continuous lathe-like cutting of the rotating cylindrical tissue block 160. This continuous blockface taping process will be detailed below. Also shown in FIG. 4A is a thin-film and adhesive blockface-application mechanism 218. This mechanism applies a thin-film coating onto the freshly cut surface of the cylindrical tissue block 160 and then applies two strips of adhesive to the tissue block 160's surface as well. This adhesive is what will secure the tape to the blockface just prior to slicing at knife 214. Final TEM-ready tissue tape is reeled up onto a take-up reel 302.

FIG. 5A is a perspective view detailing the tape-web mechanism 300 and cylindrical tissue block 160 only. The lathe body and cross-slide components have been removed for clarity. FIG. 5B shows the same mechanism, but a close-up view from behind the tissue block detailing the blockface application mechanism. FIG. 5C is a close-up view of the side of the tissue block during operation.

Starting at the top of the mechanism, a top base tape feed roll 304 supplies a continuous stream of plastic tape 305 into the mechanism. A tape hole puncher mechanism 306 punches square viewing holes into the plastic top base tape 305. The tape is driven forward by tape drive rollers 308 which maintain a slack (no tension) region 309 in the web. This slack region assures that no tension forces from the tape disturb the motion of the cylindrical tissue block 160 or the blockfack taping process.

The slack, hole-cut tape 309 is adhered to the block 160's surface at a blockface taping pressure roller 330. The timing of the hole cutting performed by the tape hole puncher mechanism 306 is synchronized to the current angle of the cylindrical tissue block 160 such that each hole will be precisely aligned directly over an embedded tissue cube 140 when the tape 309 is adhered to the block 160. A section 332 of top base tape is adhered for a quarter-turn of the block 160 before it is sliced off the block 160 at the knife 214 along with a thin ribbon 402 (detailed in FIG. 6A) of the tissue block 160. The thickness of this ribbon of tissue is set by the relative rotary speed of the lathe spindle 206 and the linear speed of the knife 214. Both speeds are constant and serve to cut off a continuous spiral ribbon of embedded tissue 402 which is already adhered to the tape 332 at the time of cutting producing a freshly microtomed ribbon of tissue adhered to top base tape 334.

Figure 6A:
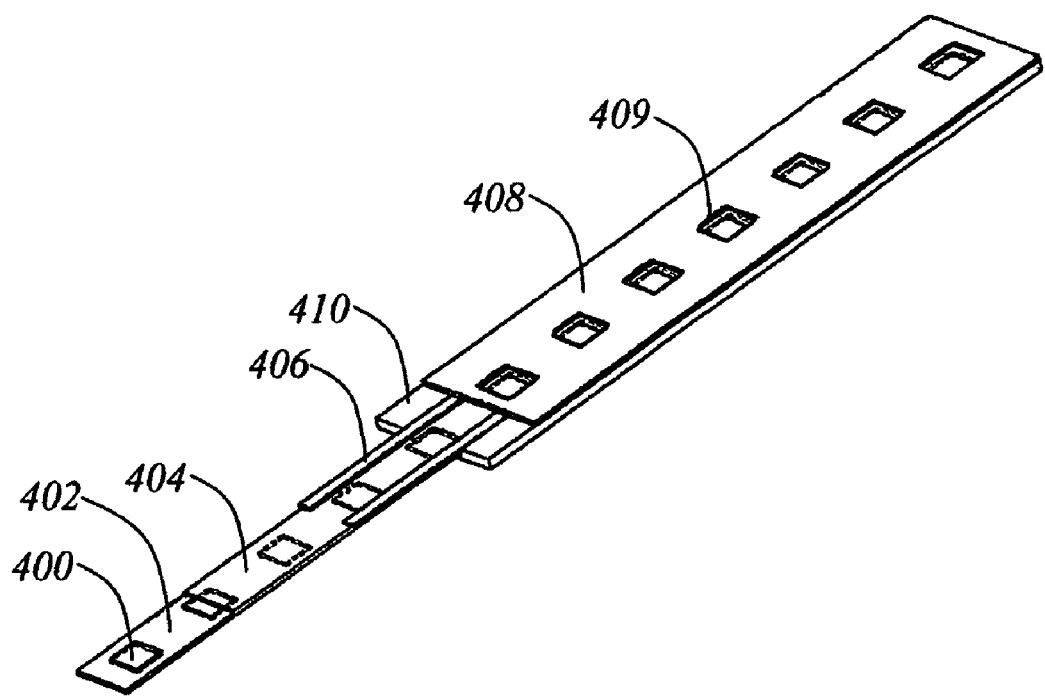
FIG. 6A is a perspective view of the final composite tape sandwich, where each layer in the composite sandwich is peeled away and labeled.

The ribbon of tissue adhered to tape 334 is reeled up by a final composite tissue tape-sandwich take-up reel 302, but before it gets there the tape 334 is driven past a bottom base tape applicator (and blowout hole mechanism) 336 that applies (prints) a covering bottom base tape 410 (detailed in FIG. 6A). The blowout hole function of 336 will be discussed later during the section on tape imaging. This produces a TEM-ready composite tape sandwich (abbreviated tissue-tape) 338 which is reeled up onto take-up reel 302.

FIGS. 5B and 5C more clearly show the blockface preparation steps leading up to the production of the adhered section of tape 332. The freshly cut surface of cylindrical tissue block 310 comes into contact with the TEM support film head 312 which lays down a thin-film on the entire surface of the block with the help of a smoothing and drying roller mechanism 314. This produces a support film coated block surface 316. This surface next conies in contact with two adhesive strip applicator heads 318 that, with the help of a smoothing and drying roller mechanism 320, lay down two strips of adhesive on the block face 322. This section of the block's surface with TEM support film and adhesive strips applied is now ready to accept the hole-cut tape 309 for blockface taping via the pressure roller 330.

Figure 6B:
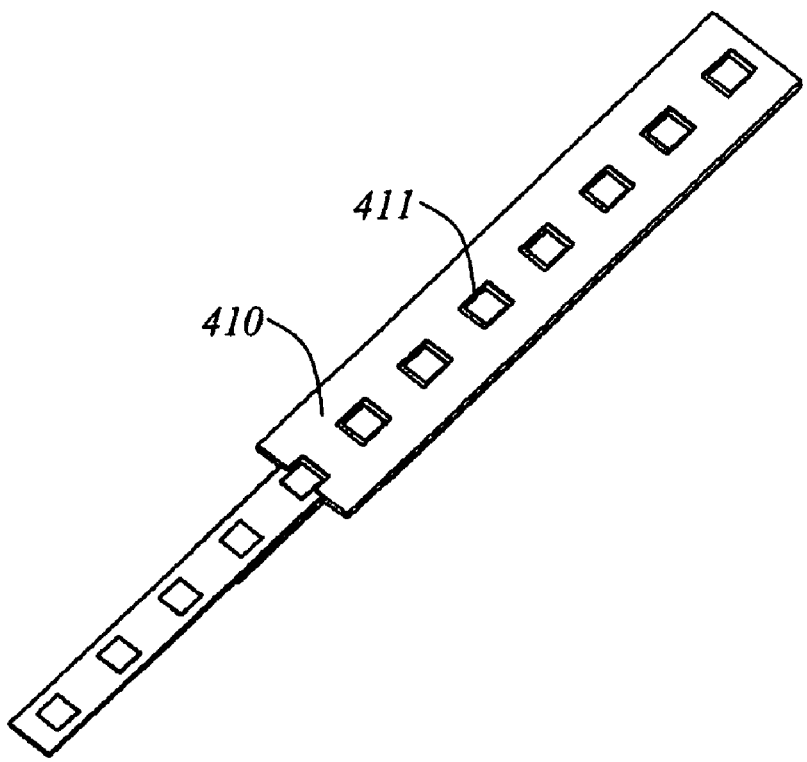
FIG. 6B is a view of the final composite tape sandwich from the underside.

FIG. 6A shows the composition of the tissue-tape 338. FIG. 6B shows the backside of the tissue-tape. In these figures, each layer in the composite sandwich has been peeled away and labeled. The tissue tape 338 consists of a composite tape-sandwich where the microtomed ribbon cut off the tissue block 402 is secured and protected between top 408 and bottom 410 base tapes. A multitude of 1 mm$^2$ microtomed tissue slices 400 (each 100 nm to 1 µm thick) are seen to be embedded in the ribbon 402. Further, this ribbon 402 is covered by a TEM support film coating 404 providing support for each tissue slice 400 across the viewing slots (holes) in tapes 408 and 410 (these holes are labeled 409 in the top tape FIG. 6A, and 411 in the bottom tape FIG. 6B). The adhesive strips 406 laid down by the applicator heads 318 just before block-face taping by pressure roller 330 are seen clearly in FIG. 6A. Notice how these strips avoid obstructing the view of the tissue slices 400 but still provide adherence between the tissue ribbon 402 and the top tape 408.

Seen in the close up view offered by FIG. 6A, one can appreciate the tissue-tape 338's similarity to the film in a movie projector. Each tissue slice 400 resides in its own frame, acting as a TEM slot grid. This analogy to the film in a movie projector can be taken further. In this form, the tissue-tape 338 can be reeled up without damage to the delicate tissue slices 400 since the slices are protected on both sides by the base tapes 408 and 410. These reels of tissue-tape can be handled and stored efficiently, and can be fed into an electron tomography tape cassette 500 (shown in FIG. 7A) for fast random access ultrastructure imaging in a standard commercial TEM.

Electron Tomography Tape Cassette Mechanical Design and Operation

Figure 7A:
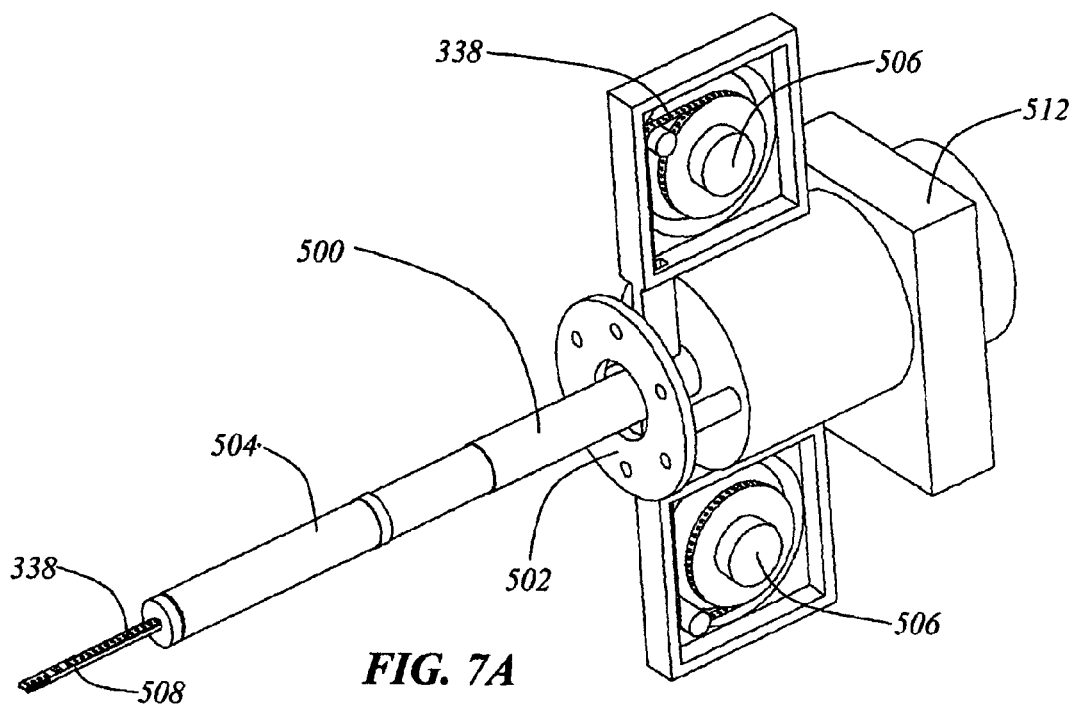
FIG. 7A is a perspective view showing the electron tomography tape cassette with side panels removed to reveal the tissue tape reels within.

FIG. 7A shows the electron tomography tape cassette 500. Side panels have been removed to reveal two tissue-tape reels 506. The electron tomography tape cassette 500 is designed to act like a standard TEM specimen stage, and thus can slide into the specimen port of a standard TEM 530 (see FIG. 8B). The main difference between the electron tomography tape cassette and a traditional TEM specimen stage is the addition of a set of tape reels and motors 506 for mounting the tissue tape 338 on, and the addition of internal mechanisms that allow the tissue tape 338 to be feed all the way out to the specimen stage's tip 508 and thus into the TEM's electron beam for ultrastructure imaging of the tissue slice 510 clamped at the stage's tip 508. There is a TEM mounting flange 502 which secures the body of the electron tomography tape cassette 500 to the side of a TEM 530. There is also a cylindrical specimen stage body 504 which slips into the vacuum port on the TEM 530 and forms a tight vacuum seal with it, yet simultaneously allows rotation around the long axis of the cylindrical specimen stage body 504. This rotation allows the incidence angle at which the electron beam impinges upon the tissue slice 510 to be varied by rotating the entire assembly of the cylindrical specimen stage body 504 and the cassette reels and motors 506 relative to the mounting flange 502 (see FIGS. 8C, 8D, and 8E). This rotation of the cylindrical specimen stage body 504 relative to the flange 502 is driven by a drive motor 512. Changing this angle of incidence allows for 3D reconstruction of the tissue slice having better resolution in depth than the slice thickness would allow if only 2D (non-tilt series) imaging were performed, and is a standard technique in electron microscopy today.

Figure 7B:
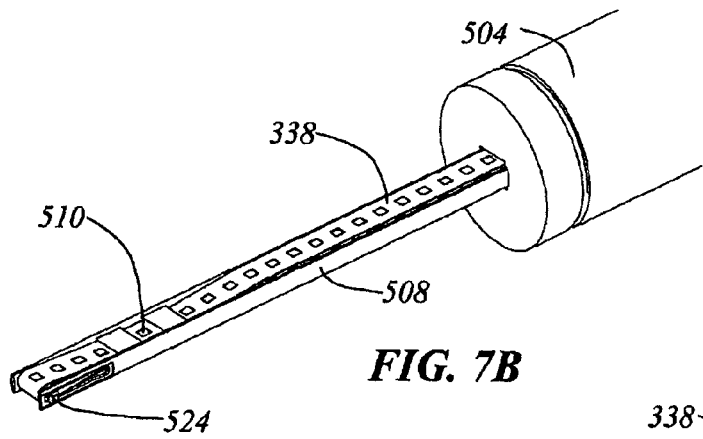
FIG. 7B is a close-up view of the specimen stage tip of the electron tomography tape cassette.
Figure 7C:
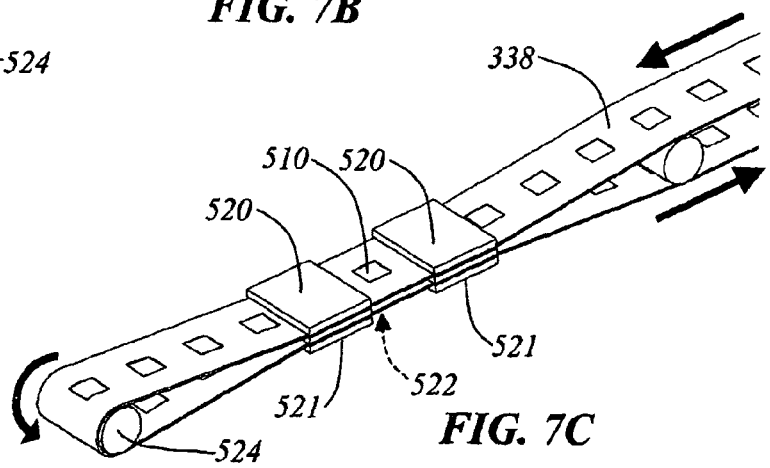
FIG. 7C is a close-up view of the specimen stage tip of the electron tomography tape cassette where the sides of the tip have been removed to reveal the tape path and clamping mechanism within.

FIG. 7B shows a close-up view of the specimen stage tip 508. FIG. 7C is a close-up view of the specimen stage tip 508 where the sides of the tip have been removed to reveal the tape path and clamping mechanism within. The tissue-tape 338 wraps around a pulley 524 at the very front of the tip 508. During operation, the tape drive motors 506 reel the tissue tape 338 such that the tissue slice to be imaged 510 is centered between two top clamps 520 and is thus inline with the TEM's electron beam. These two top clamps 520 then engage, securing that section of tissue-tape containing the slice to be imaged 510 stably in position. The pulley 524's position is then adjusted electronically to lengthen or shorten the section of tape 338 between the top clamps 520 and a pair of bottom clamps 521 in order to bring a blowout hole 522 into position between the two bottom clamps 521. These bottom clamps 521 are then engaged to secure the entire tape 338 for imaging.

This blowout hole 522 is one of a multitude of blowout holes spaced periodically throughout the tape 338. These holes are made within the automatic taping lathe microtome's bottom tape applicator and blowout hole mechanism 336 by simply directing a puff of air at the fragile section of sliced ribbon 402 in periodically spaced frames of the tissue tape 338. Recall that a few tooth-indentation cavities 132 are specifically left empty of tissue cubes 140 during the embedding process for this reason. Thus, the final axle-mounted tissue block 160 had three tissue-free regions 162 around its periphery (see FIG. 3C). These holes 522 are purposely blown out to allow the wrapped around section of the tissue tape 338 which resides between the bottom clamps 521 to not obstruct the imaging of the tissue slice 510 directly above it. The cutaway view of the specimen stage tip 508 in FIG. 7C shows both sets of clamps 520 and 521 engaged securely holding a single slice of tissue 510 in position inline with the TEM's electron beam. Directly below this tissue slice 510 is a blowout hole 522 in the tissue tape 338 and thus only the particular slice to be imaged 510 will be seen by the TEM's electron beam.

FIG. 8A shows the electron tomography tape cassette 500 with arrows drawn to display the main degrees of freedom of movement allowed by the mechanism. The reels of tissue tape 506 can rotate in synchrony to bring any desired slice of tissue in the tape out to the specimen tip and thus into the electron beam for imaging. Exact positioning of the field of view is set by driving the whole tip mechanism along the two degrees of freedom perpendicular to the electron beam's cavity (depicted by arrows shown near tip). Also, the entire cassette and stage body 504 can rotate relative to the TEM mounting flange 502 as described below.

FIG. 8B depicts a stylized transmission electron microscope (TEM) with the electron tomography tape cassette inserted into its specimen port. The tape cassette (with cassette covers, which were removed in previous view, installed) is hermetically sealed and can thus share the TEM's vacuum via its seal along the stage's body 504. The tissue tape 338 within the tape cassette 500 is electronically advanced using reel motors 506 to bring a particular tissue slice 510 to be imaged inline with the TEM's electron beam. Clamps (520 and 521) engage to allow stable unobstructed viewing of the slice 510. Any X-Y motions of the stage are now performed to address a small section within the slice (using standard X-Y specimen stage motors present in the electron tomography tape cassette 500 but, for clarity, not depicted here). A tomographic tilt-series (a set of 121 2D electron micrograph images of the tissue slice 510) can be taken by stepping the incidence angle in 1° increments from −60° to +60°.

In FIGS. 8C, 8D, and 8E the manner in which the body of the electron tomography tape cassette rotates relative to the TEM mounting flange 502 is depicted. Those three figures show the tape cassette mechanism at three different incidence angles (−60°, 0°, and +60° respectively).

At each angle, a 2D electron micrograph is produced and all 121 of these images are fed into a standard electron tomographic volume reconstruction algorithm in order to compute a 3D voxel volume digital image of the particular piece of tissue 510 under examination. The system is designed such that any of the multitude of tissue slices in the tissue-tape 338 loaded into the electron tomography tape cassette 500 can be randomly and automatically accessed for 2D or 3D tomographic imaging (at ultrastructure resolution) without ever cracking the vacuum of the TEM. Thus, this avoids any time-consuming manual intervention in the imaging process.

Summary of Preferred Embodiment

This concludes the description of the preferred embodiment of the automatic taping lathe-microtome and associated methods and apparatuses for the automated production, collection, handling, and imaging of large numbers of serial tissue sections. Hopefully it can now be appreciated that this disclosed set of methods and apparatuses addresses many (if not all) aspects pertaining to the true automation of the process of 3D serial reconstruction of biological (especially neural) tissue. The methods and apparatuses disclosed cover changes to the standard practices ranging from the initial tissue embedding process, through the microtomy process, and all the way to the TEM imaging process. They form an integrated set of process and mechanical design changes meant to allow 3D ultrastructure reconstructions of large volumes of neural tissue to be reliably and efficiently produced. The ability to automate the production of such large-scale ultrastructure reconstructions of neural tissue would prove incredibly important to the neuroscience research community just as the ability to automate the sequencing of large stretches of DNA has already proved incredibly important to the genetics research community over the past decade.

Alternative Embodiments of the Automatic Taping Lathe-microtome

The following describes some alternative embodiments for the automatic taping lathe-microtome. The following descriptions of alternative embodiments of the invention are presented for the purposes of illustration and description. They are not intended to be exhaustive or to limit the invention to the precise form disclosed.

These alternative designs involve variations on the blockface taping and tissue collection processes. These designs are depicted in a series of schematic side views in FIGS. 9A through 9D. The preferred embodiment is re-represented in FIG. 9E in this same schematic form to further promote ease of comparison.

Figure 9A:
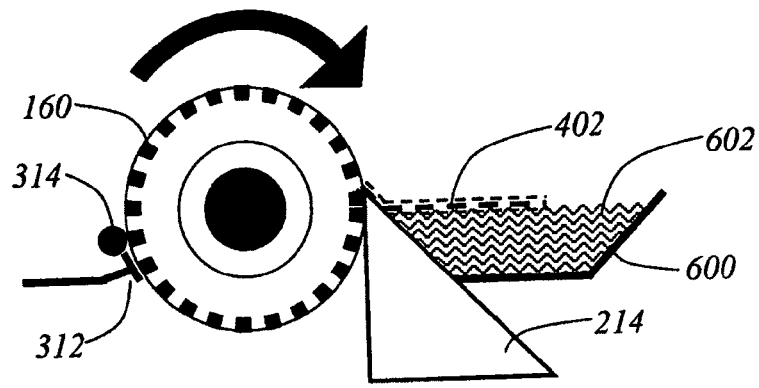
FIG. 9A is a schematic side view of alternative embodiment #1.

FIG. 9A shows a minimalist core design (alternative design #1) of the lathe-microtome. The axle-mounted cylindrical tissue block 160 is rotated against the knife 214 in order to liberate a thin ribbon of tissue slices in embedding medium 402. There is no blockface taping in this design (just thin-film support film deposition by 312 and 314) and so a boat 600 filled with water 602 must be attached to the knife 214 in order to collect the fragile un-taped tissue ribbon 402 as it comes off the knife. In this design, once the tissue ribbon becomes longer than the water boat, manual collection of the tissue ribbon is required, thus this design cannot be considered truly automated.

Figure 9B:
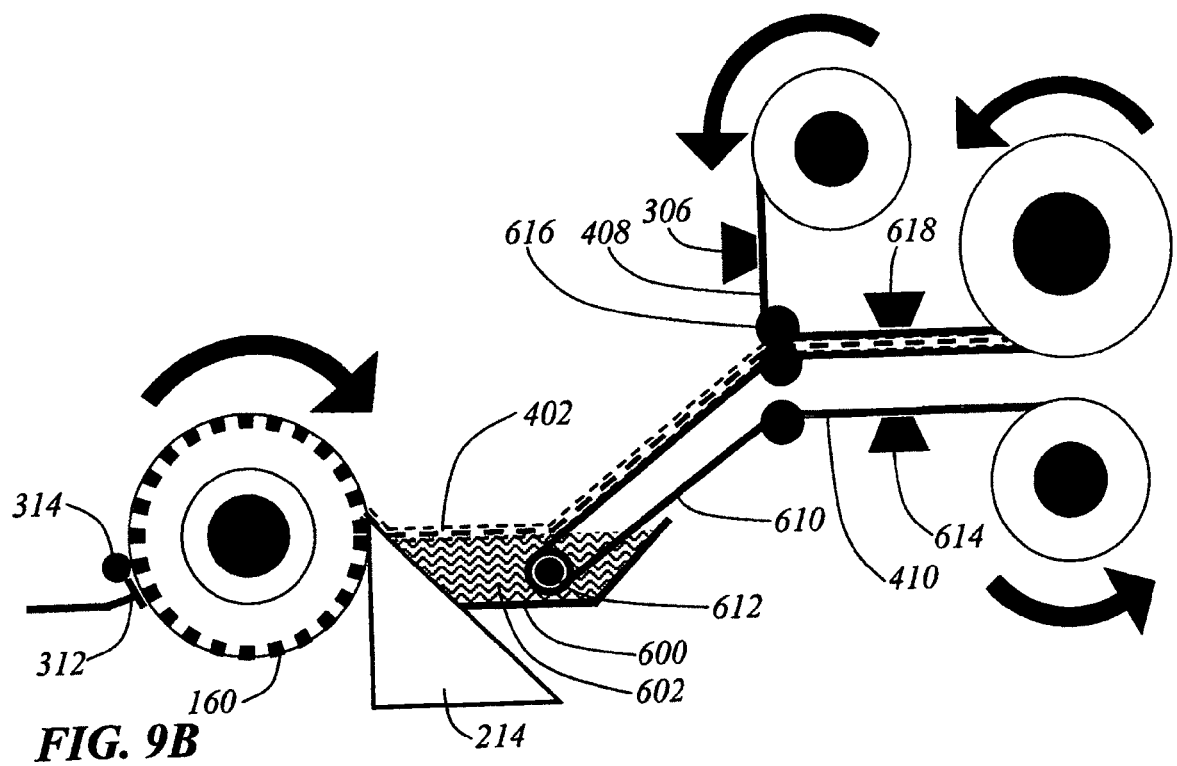
FIG. 9B is a schematic side view of alternative embodiment #2.

FIG. 9B show alternative design #2. This is a modification to the minimalist core design in which a submerged conveyor belt 610 is made up of the bottom base tape 410 looped around a pulley 612 firmly attached to the knife's water boat and submerged in its water 602. This arrangement allows the fragile floating tissue ribbon 402 to be gently and continuously lifted out of the water by the conveyor belt 610 as shown in the figure. A bottom base tape hole punching mechanism 614 punches viewing holes in the bottom base tape, and its punches are synchronized with the angle of the tissue block 160 such that each tissue slice 400 in the tissue ribbon 402 resides over a viewing hole. The top tape 408 after having similar viewing holes punched in it by hole puncher 306 is aligned and pressed onto the top of the conveyor belt by pressure roller 616. This produces a tape-sandwich which can be sealed by a sealing mechanism (e.g. a heated pressure roller) 618 before finally being reeled up as a finished TEM-ready tissue tape. This design is fully automated and produces a tissue tape-sandwich capable of automated imaging using the electron tomography tape cassette 500. This design (FIG. 9B) does not employ blockface taping meaning that there is a place in the mechanism where a fragile, freely-floating ribbon of tissue 402 is unsecured by any base tape. This reduces the reliability of the design, but it also reduces its complexity by eliminating blockface taping.

Figure 9C:
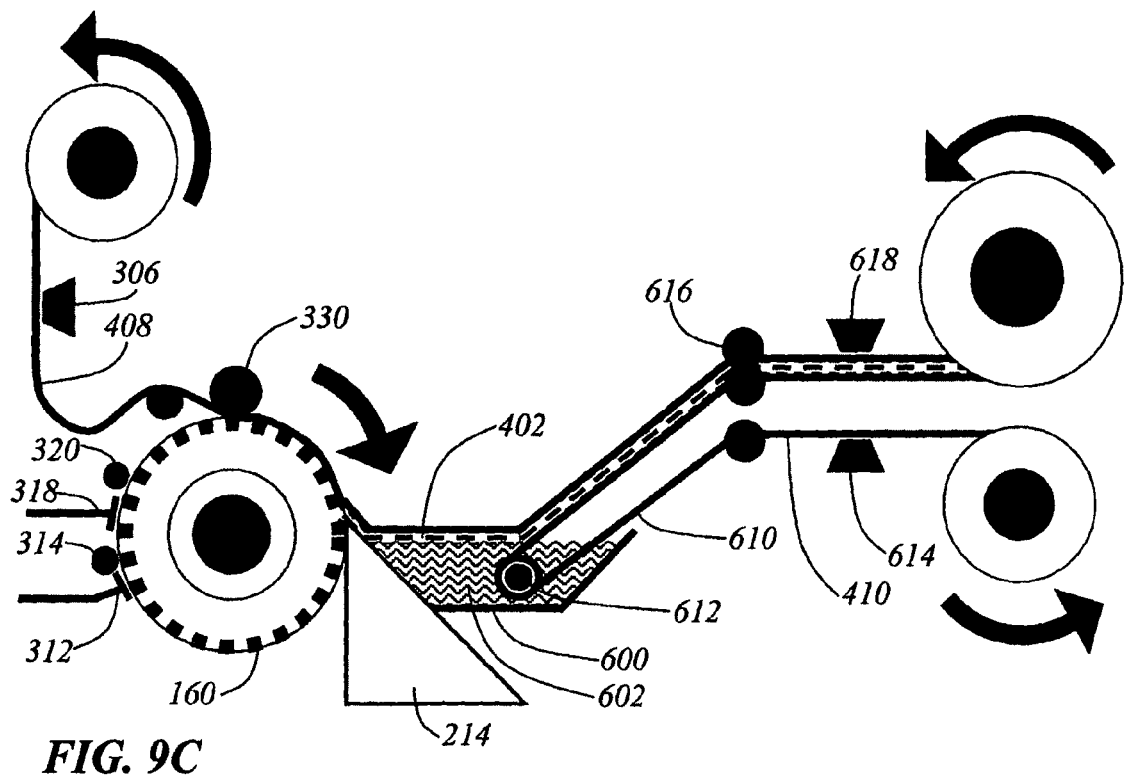
FIG. 9C is a schematic side view of alternative embodiment #3.

FIG. 9C shows alternative design #3 which simply adds blockface taping to the submerged conveyor-belt design. This design is similar to the preferred embodiement's in its use of a blockface taping pressure roller 330 adhering the top base tape 408 directly to the blockface before cutting. In this way there is never a fragile, unsupported tissue ribbon. This design has both the advantage of blockface taping tissue support at the knife and the advantage of a knife water boat to prevent friction-induced damage with the knife. It, however, suffers from the complexity of both a water boat and blockface taping mechanism.

Figure 9D:
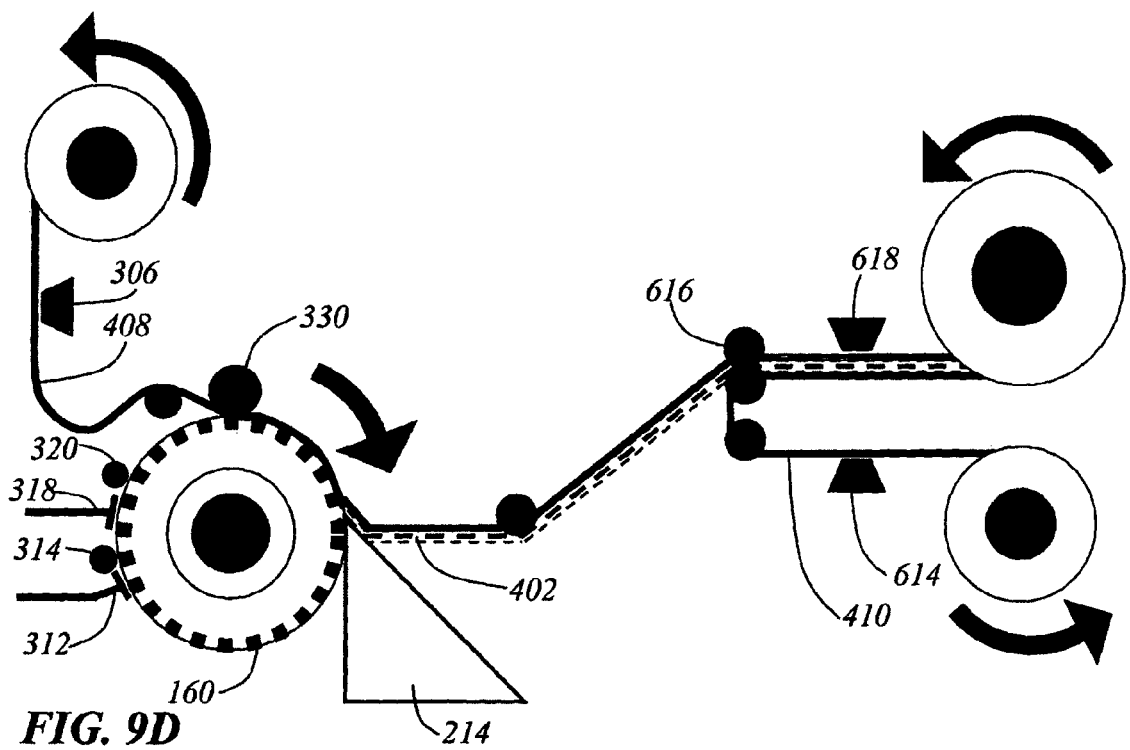
FIG. 9D is a schematic side view of alternative embodiment #4.

FIG. 9D shows alternative design #4 in which the water boat has been removed and the conveyor-belt formed by the bottom base tape is no longer submerged. The blockface taping has provided enough support for the tissue ribbon 402 coming off the knife 214 such that the water boat support can be eliminated.

Figure 9E:
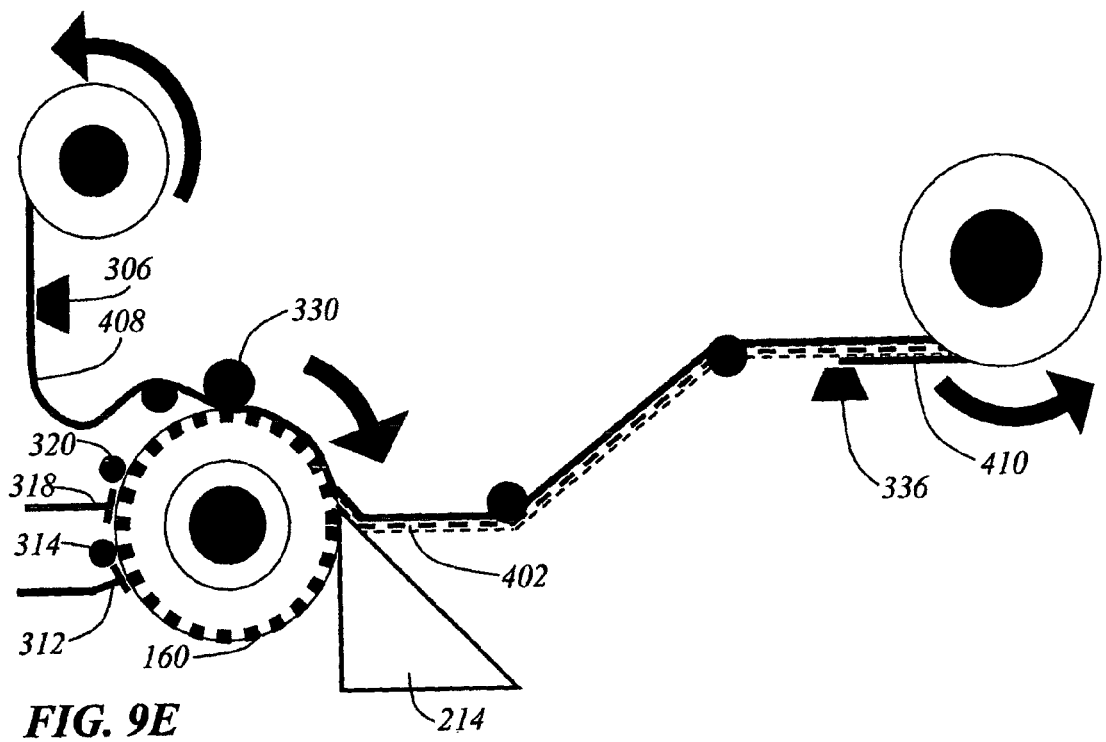
FIG. 9E is a schematic side view of the preferred embodiment.

Finally, FIG. 9E shows the preferred embodiment in the same schematic manner as the just described alternative designs. In it, the conveyor-belt made up of the bottom tape is replaced by a printing head 336 that manufactures the bottom base tape 410 in situ. This simplifying change can be tolerated if the final tissue tape-sandwich still has sufficient strength provided now only by the top tape. The in situ manufactured bottom tape is then only acting as a relief to protect the tissue from friction damage during reel-up operations.

Another alternative embodiment, which is not depicted in the figures, is to forgo cutting viewing holes in the top and/or bottom base tapes within the microtome, and instead, as a later step, etch these holes using an acid to reveal the tissue slices within. If the top and bottom base tapes are made of a solid material (preferably a metal such as copper) and no holes are cut in the microtome in these tapes, then the composite tape sandwich taken-up on the final take-up reel 302 will not be ready for imaging since the tissue slices between the top and bottom tapes will be hidden by the overlying tapes. This tape-sandwich can then be put through an etching machine where a mask is placed around each section of tape covering up all areas of tape except those having tissue directly beneath. Then the tape is exposed to an etchant (acid in the case of metal tapes) that will dissolve the parts of the top and bottom tape directly above and below each tissue slice. The etchant is chosen so as not to damage the delicate tissue slice which is revealed via the etching process. The advantage of this viewing hole etching method is that it allows the blockface taping step to proceed with a solid tape instead of one with viewing holes. This implies that the tissue slice being cut can be supported across its entire width during the cutting procedure.

Once again, these descriptions of alternative embodiments of the invention were presented for the purposes of illustration and description. They are not intended to be exhaustive or to limit the invention to the precise form disclosed. Many modifications and variations are possible. It is intended that the scope of the invention be limited not by this detailed description of the preferred embodiment or the alternative embodiments, but rather by the claims section to follow.

ADVANTAGES AND CONCLUSIONS

We will now summarize the key advantages of the present invention over the current state-of-the-art in serial section production, collection, handling, and imaging.

Advantage #1: The present invention allows for the processing of multiple tissue cubes simultaneously by embedding a multitude of tissue cubes in a single axle-mounted tissue block.

Advantage #2: The novel design of the automatic taping lathe-micotome departs most radically from current sliding, rotary, and disc microtome designs in that it makes possible a smooth, continuous slicing motion where the knife never disengages from the tissue block during operation. This offers a distinct improvement in the fundamental reliability of the slicing operation in that a continuous, non-disengaging, lathing action can be made much more stable than current microtomes which use a discontinuous ratcheting motion. This is a crucial improvement if thousands of thin tissue slices are to be produced without error in a fully automatic manner.

Advantage #3: Because the slicing action of the automatic taping lathe-microtome proceeds in a smooth, continuous manner (where the knife never disengages from the tissue block during operation) it is now possible to include in the design continuous blockface taping where the tape never disengages from the block. This represents a dramatic simplification in the process of blockface taping over any proposed automation of blockface taping in discontinuous motion microtomes (which by their nature necessitate the tape to engage and disengage during any blockface taping operation as well).

This blockface taping technique, along with the novel technique of blockface deposition of the TEM support film, strengthens the tissue sections before cutting by making the thin slice required for TEM work appear thicker and stronger before the time of slicing. As importantly, continuous blockface taping also allows the freshly liberated tissue slice (ribbon) to be collected automatically as part of the tissue tape-sandwich.

Advantage #4: All aspects of the current invention are centered on producing and using the TEM-ready tissue tape-sandwich 338. This novel collection, storage, and imaging medium has no direct analogy in current electron microscopy practice. It has the potential to replace the water boat as a slice-collection device and the TEM slot grid as a sample holding device thus eliminating the arduous manual steps of water boat slice retrieval and grid mounting. Unlike the storage tape proposed by Bolles which only allows light-microscopic imaging, the tissue tape-sandwich in this invention allows for TEM viewing by integrating a series of viewing holes into both top and bottom base tapes and by using the novel technique of blockface deposition of the TEM support film.

Advantage #5: Finally, this TEM-ready tissue tape-sandwich containing many thousands of individual tissue slices (representing perhaps many cubic millimeters of neural tissue volume) can be loaded, all at once, into a single TEM using the novel electron tomography tape cassette. That invention allows the tissue tape to be threaded through a standard TEM's electron beam in a fashion similar to film in a movie projector. This allows any tissue section on the entire tape (i.e. any point within the sliced volume) to be randomly accessed for ultrastructure imaging without forfeiting the time needed to crack the TEM's vacuum and repumping.

The truly automated production, handling, storage, and random-access imaging of TEM-ready serial tissue sections made possible by the disclosed innovations could even make possible new ways of thinking about how TEM imaging is applied to neuroscience research. For instance, it might make possible the establishment of tissue-tape libraries storing the volume of entire mammalian brains and containing vastly more tissue slices than could ever be methodically imaged in total. Such tape libraries would instead be made available online to the entire research community for random-access imaging on request. One could as well imagine automated image-sequence direction algorithms putting the random-access imaging capability to use for following and imaging multi-scale structures of interest such as the torturously long, thin, and complexly intertwined axonal and dendritic processes of the brain. These could be traced and imaged across multiple tissue slices contained on the same tape all without user intervention. The benefits to the neuroscience research community of such efficient multi-scale (ultrastructure to whole brain) imaging could be enormous.

What is claimed is:

1. A method for processing a tissue sample, the method comprising:
    contacting the tissue sample with a cutting surface so as to liberate a thin tissue section that includes at least a portion of the tissue sample; and
    automatically collecting the thin tissue section on to a support tape that is adapted for electron microscopy imaging, wherein the support tape is conductive.

2. The method of claim 1, wherein the support tape comprises metal.

3. The method of claim 1, wherein the support tape is adapted to permit electrons to travel along a line between an upper region of the support tape and a lower region of the support tape.

4. The method of claim 3, wherein the support tape includes holes that permit electrons travel between the upper region and the lower region of the support tape.

5. The method of claim 1, wherein upon placement of the support tape in a chamber of an electron microscope and upon subsequent bombardment of electrons on to the support tape, the electrons are permitted to travel freely along a surface of the support tape so that the support tape does not exhibit charging.

6. The method of claim 1, wherein the thin tissue section is less than 1 micron in thickness.

7. The method of claim 6, wherein the thin tissue section is between about 100 nm and about 1 micron in thickness.

8. The method of claim 1, further comprising automatically collecting a plurality of thin tissue sections liberated from the tissue sample on to the support tape, the plurality of thin tissue sections defining an original volume of the tissue sample.

9. The method of claim 8, further comprising imaging the plurality of thin tissue sections to produce a plurality of tissue section images.

10. The method of claim 9, further comprising rendering a three-dimensional reconstruction of the original volume of the tissue sample from the plurality of tissue section images.

11. The method of claim 1, wherein contacting the tissue sample with a cutting surface comprises contacting the tissue sample with an ultramicrotome-quality knife.

12. The method of claim 1, wherein contacting the tissue sample with a cutting surface so as to liberate a thin tissue section comprises slicing off a thin tissue section from the tissue sample.

13. A method for processing a tissue sample, the method comprising:
   contacting the tissue sample with a cutting surface so as to liberate a thin tissue section that includes at least a portion of the tissue sample, the thin tissue section being less than 1 micron in thickness; and
   automatically collecting the thin tissue section on to a support tape, wherein the support tape is conductive.

14. The method of claim 13, wherein the thin tissue section is between about 100 nm and 1 micron in thickness.

15. The method of claim 13, wherein the support tape is adapted for electron microscopy.

16. The method of claim 13, further comprising automatically collecting a plurality of thin tissue sections liberated from the tissue sample on to the support tape, the plurality of thin tissue sections defining an original volume of the tissue sample.

17. The method of claim 16, further comprising imaging the plurality of thin tissue sections to produce a plurality of tissue section images.

18. The method of claim 17, further comprising rendering a three-dimensional reconstruction of the original volume of the tissue sample from the plurality of tissue section images.

19. The method of claim 13, wherein contacting the tissue sample with a cutting surface comprises contacting the tissue sample with an ultramicrotome-quality knife.

20. The method of claim 13, wherein contacting the tissue sample with a cutting surface so as to liberate a thin tissue section comprises slicing off a thin tissue section from the tissue sample.

* * * * *